United States Patent [19]

Root

[11] Patent Number: 5,650,323

[45] Date of Patent: Jul. 22, 1997

[54] SYSTEM FOR GROWING AND MANIPULATING TISSUE CULTURES USING 96-WELL FORMAT EQUIPMENT

[75] Inventor: David Root, Lexington, Mass.

[73] Assignee: Costar Corporation, Cambridge, Mass.

[21] Appl. No.: 721,250

[22] Filed: Jun. 26, 1991

[51] Int. Cl.$^6$ .................................................. C12M 3/00
[52] U.S. Cl. ...................... 435/284.1; 210/238; 422/101
[58] Field of Search ........................ 435/284, 285, 435/300, 301, 311, 297, 298; 422/101, 102; 210/238, 406, 450, 482; 220/800, 803, 806, 807

[56] References Cited

U.S. PATENT DOCUMENTS

| | | | |
|---|---|---|---|
| 4,626,509 | 12/1986 | Lyman | 435/287 |
| 4,770,993 | 9/1988 | Ghosh-Dastidar | 435/7 |
| 4,871,674 | 10/1989 | Matsui et al. | 435/284 |
| 4,895,706 | 1/1990 | Root et al. | 436/178 |
| 4,948,975 | 8/1990 | Erwin et al. | 250/361 |
| 5,009,780 | 4/1991 | Sarrasin | 210/238 |
| 5,026,649 | 6/1991 | Lyman et al. | 435/284 |
| 5,035,866 | 7/1991 | Wannlund | 422/102 |
| 5,047,215 | 9/1991 | Manns | 422/101 |
| 5,061,639 | 10/1991 | Lung et al. | 436/164 |
| 5,082,628 | 1/1992 | Andreotti et al. | 422/82.08 |

FOREIGN PATENT DOCUMENTS

| | | |
|---|---|---|
| 170898 | 9/1951 | Austria . |
| 0183973 | 6/1986 | European Pat. Off. . |
| 1003489 | 2/1957 | Germany . |
| 370873 | 9/1963 | Switzerland . |
| 2155948 | 10/1985 | United Kingdom . |
| WO87/05533 | 9/1987 | WIPO . |

OTHER PUBLICATIONS

1990 Costar Catalog, pp. 4–5.
Culture of Animal Cells by R.I. Freshney, published in 1983 by A. Liss, New York, NY 10011, pp. 61–62.

Primary Examiner—Robert J. Warden
Assistant Examiner—Krisanne M. Thornton
Attorney, Agent, or Firm—George L. Greenfield

[57] ABSTRACT

A laboratory research tool for conducting a variety of procedures including cell and tissue culture techniques includes a multi-well cluster plate, a filter plate that has one or more filter wells that extend into the wells of the cluster plate, a cover and a reservoir that can be used with auxiliary equipment designed for use with standard 96-well format cluster plates. The system allows multiple tissue samples to be grown and manipulated simultaneously.

26 Claims, 4 Drawing Sheets

SYSTEM FOR GROWING AND MANIPULATING TISSUE CULTURES USING 96-WELL FORMAT EQUIPMENT

INTRODUCTION

This invention relates to laboratory research tools for conducting a variety of procedures including cell and tissue culture techniques and more particularly comprises a multi-well cluster dish system which can be used with auxiliary equipment designed for use with standard 96-well cluster plate formats. The system of this invention allows multiple tissue samples to be grown and/or manipulated simultaneously, and is a further development of the system shown in copending applications Ser. No. 06/841,562 filed Mar. 20, 1986 entitled APPARATUS FOR GROWING TISSUE CULTURES IN VITRO that is to issue as U.S. Pat. No. 5,026,649 on Jun. 25, 1991 and Ser. No. 07/695,300 filed May 3, 1991 with the same title. Those applications are assigned to the assignee of the present application and are incorporated herein by reference. The disclosures of those applications are incorporated herein by reference.

BACKGROUND

Cell and tissue culture techniques are becoming increasingly more important to basic and applied life science research. The development of culture containers and cell attachment substrates have been driven by the need to produce an environment that resembles the in vivo state as closely as possible. As a result, permeable supports including microporous membranes in a variety of configurations and devices, have become the standard method for the culture of polarized cells. Significant improvements in experimental design have resulted because permeable membrane filters permit cells to feed basolaterally and thereby carry out metabolic activities in a more natural fashion.

Membrane filters have been used as cell growth substrates since the 1950's and the transfilter mesonephric induction studies of Grobstein. Adapted over the years to a variety of cell types and numerous applications, porous membrane filters are now recognized as providing significant advantages over solid, impermeable cell growth substrates. For polarized structures such as epithelial cells, the use of permeable supports allows cells to be studied under more natural conditions. Cellular differentiation proceeds to higher levels resulting in cells that morphologically and functionally better represent their in vivo counterparts.

Cellular activities such as transport, absorption and secretion can also be studied under more natural conditions since cells grown on filters provide convenient, independent access to apical and basolateral plasma membrane domains.

The use of permeable support systems for cell culture has proven to be a valuable tool in the cell biology laboratory.

In prior application Ser. No. 06/841,562 supra, one commercially successful system for growing tissue cultures is shown. Individual filter wells are shown as used in the wells of multi-well cluster plates. That system, however, is not suitable for use with the extensive amount of auxiliary equipment developed to handle multi-well cluster plates in the standardized 96-well format.

Industry standard microtest cluster plates are laid out with 96 wells in an 8×12 matrix (mutually perpendicular 8 and 12 well rows) with a spacing of 0.355 inches between the center lines of rows both in the x and y directions. In addition, the height, length and width dimensions of the microtest 96-well plates are standardized. This standardization has resulted in the development of a large amount of auxiliary equipment being developed specifically for the 96-well formats. The equipment includes devices that load and unload precise volumes of liquid in multiples of either 8, 12, or 96 wells at a time. In addition, equipment is available to transmit light through the individual wells and to read colorimetric changes or chemiluminescence in individual wells (as a result of tests performed in each well). Some of this equipment is automated and instrumented to record, analyze and manipulate the data recorded.

The present invention includes multi-well plates having wells of substantially greater diameter and volume than the wells in the standardized 96-well plates but nevertheless are capable of being used with the equipment designed for the 96-well format. More particularly, the present invention includes a 48-well plate wherein the length, width and height of the plate is identical to the industry standard established for 96-well plates. The well diameters of the 48-well plate are maximized by staggering the wells in adjacent rows and the coincidence of the walls of adjacent wells at their points of tangency.

The present invention also includes filter plates composed of a single filter well or an array of 4, 8, 24 or 48 wells whose formats conform to the format of the multi-well cluster plate of this invention and sized so that they may extend into the wells (reservoir wells) of the cluster plate. The filter plates include means for positioning the filter wells in selected positions within the wells of the cluster plate so as to minimize capillary action between the filter and reservoir well walls and to space the filters well a preselected distance above the bottom walls of the reservoir wells. The filter plates also include means to provide access to the interior of the filter wells and the lower portion of the reservoir wells so that liquid may be introduced in precise quantities to those regions. In accordance with one embodiment of this invention, individual filter wells may be broken away from the others in the filter plate for separate analysis.

The system of this invention also includes a common reservoir that receives all of the filter wells of the filter plate so that tissue culture monolayers may be grown in multiples prior to use of the filter plate with the multi-well cluster plate of the present invention for analysis on 96-well format auxiliary equipment.

In accordance with the present invention, the 48 wells of the multi-well plate are arranged in 12 rows of 4 wells each, and the center lines of the 12 rows are spaced apart the same distance, as the spacing between the rows of wells in the standard 96-well plate, that is, 0.355 inches. The centers of the four wells in each row are spaced apart twice that distance, namely, 0.710 inches, and the wells in adjacent rows are offset from one another so that the centers of the wells in a particular row are aligned with the midpoint between the centers of adjacent wells in the adjacent rows. In this fashion, the centers of the wells in alternate rows align with the odd and even-numbered wells of corresponding rows in the 96-well format. The arrangement of the wells allows their diameters to be maximized to approximately 1.5 times the well diameter in the standard 96-well cluster plates. The large wells of the plate in turn maximize the clearance with the walls of the filter wells in the system so as to avoid capillary action. The system also enables 96-well ELISA test readers to be used in combination with multiple filter wells for applications such as chemotaxis studies, migration assays, cell uptake analysis, diagnostic tests where membranes are used for separation, sorting, affinity binding, etc. The contents of the entire filter well and reservoir well, may be read depending upon the requirement of the assay.

3

The present invention will be better understood and appreciated from the following detailed description read in connection with the accompanying drawings in which:

BRIEF FIGURE DESCRIPTION

Figure 2:
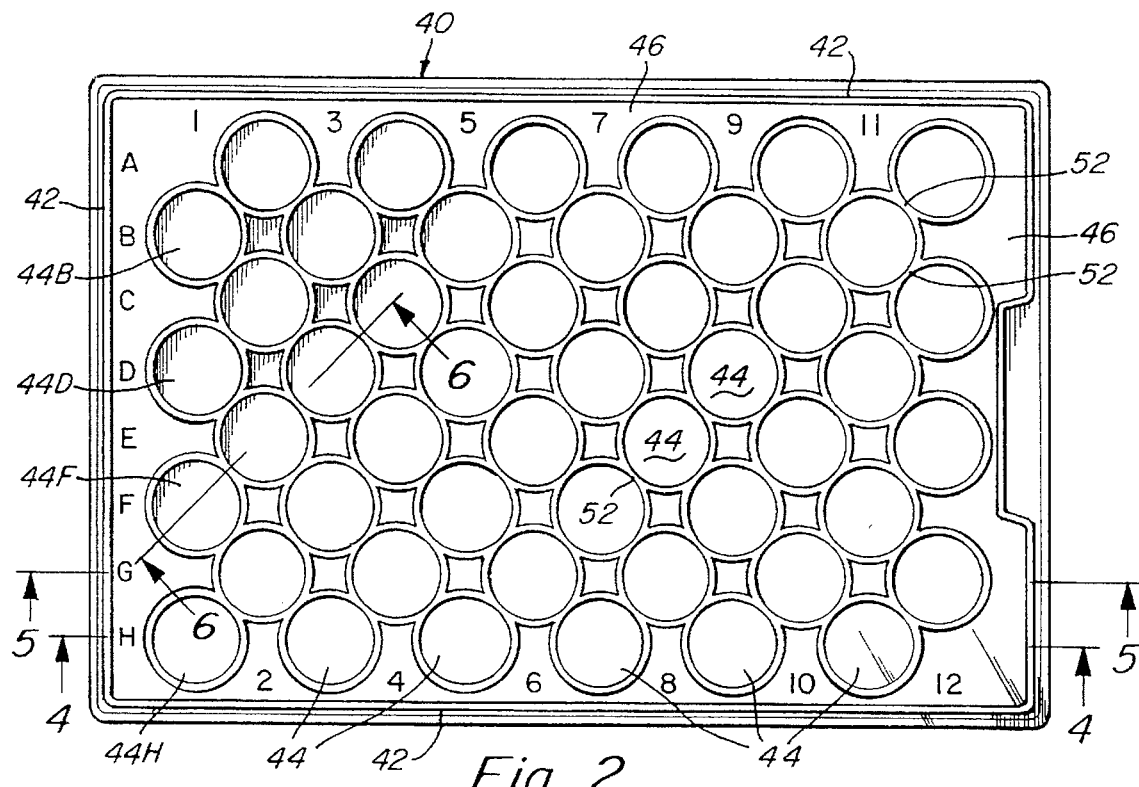
FIG. 2 is a plan view of a 48-well cluster plate made in accordance with the present invention.
Figure 3:
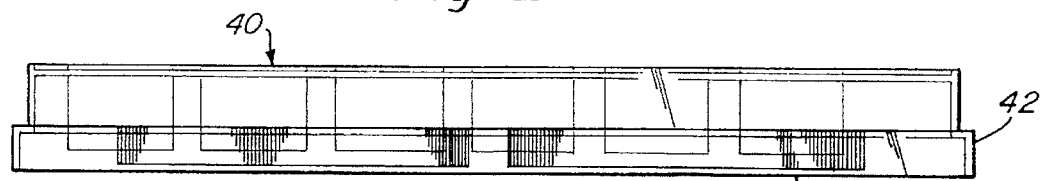
FIG. 3 is a side elevation view of the 48-well cluster plate shown in FIG. 2.
Figure 5:
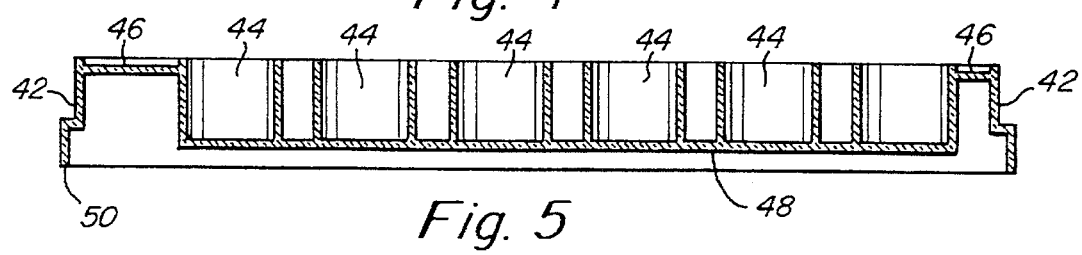
Figure 6:
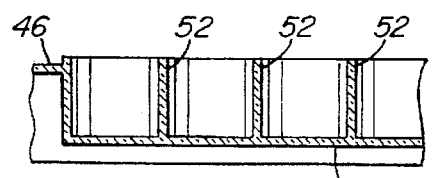
Figure 7:
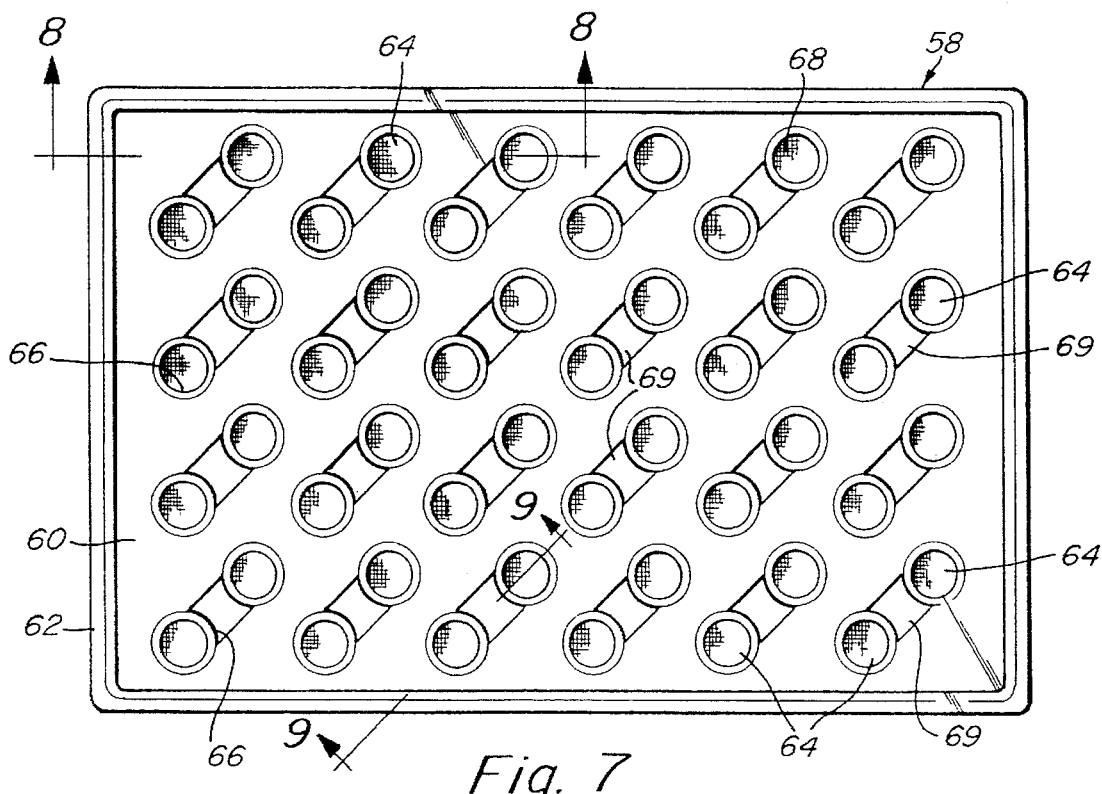
Figure 8:
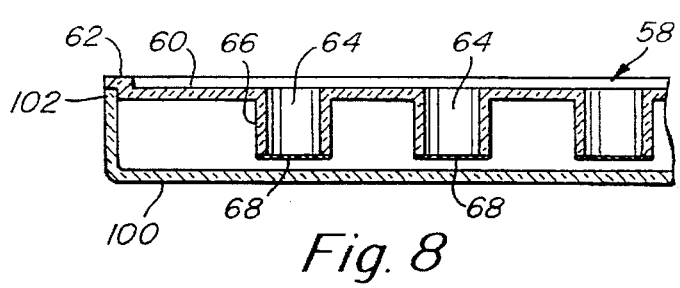
Figure 9:
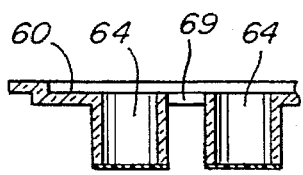
Figure 9A:
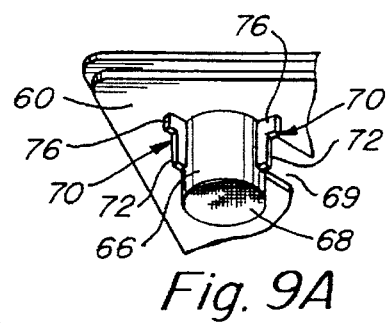
Figure 10:
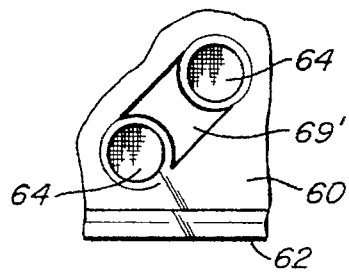
Figure 11:
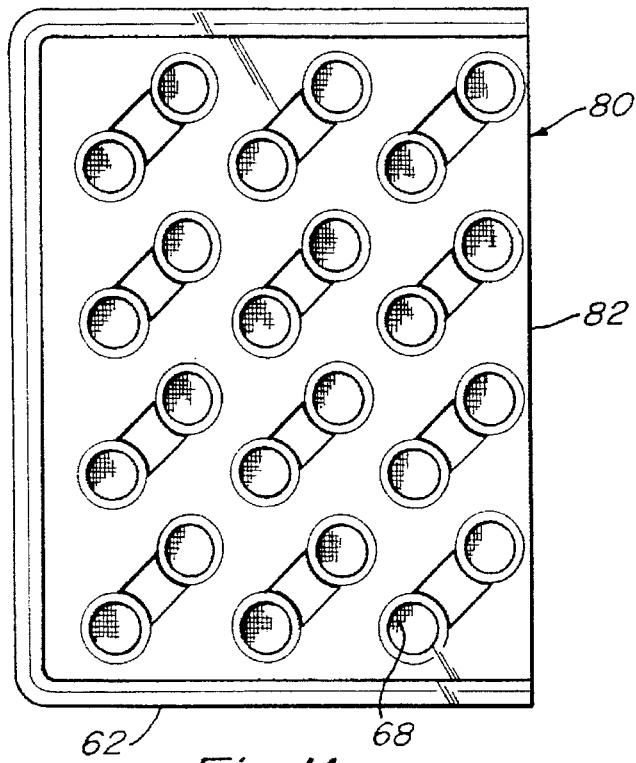
Figure 12:
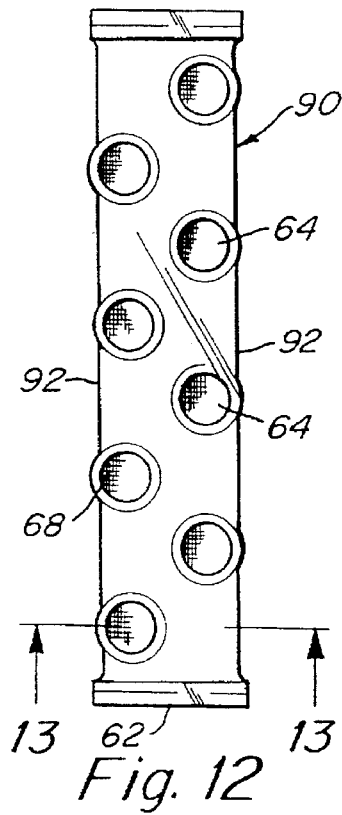
Figure 13:
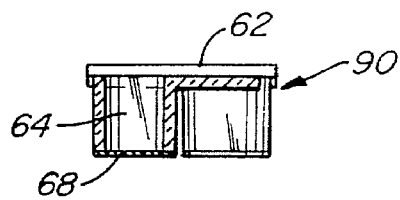
Figure 14:
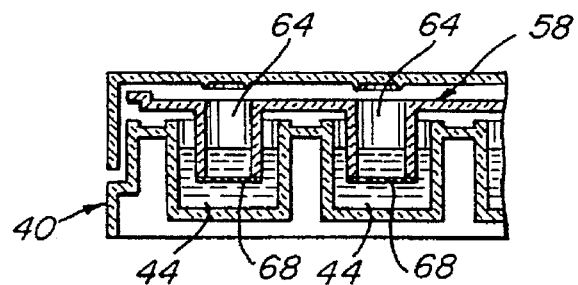

FIGS. 5 and 6 are fragmentary cross-sectional views of the cluster plate taken along the section lines 5—5- and 6—6 in FIG. 2;

FIG. 7 is a plan view of a filter plate with 48 filter wells made in accordance with the present invention;

FIG. 8 is a fragmentary cross-sectional view of the filter plate taken along the section line 8—8 in FIG. 7 and further along with an undivided media reservoir beneath it;

FIG. 9 is a fragmentary cross-sectional view of the filter plate taken along the section line 9—9 in FIG. 7;

FIG. 9A is a fragmentary perspective view of one well of the filter plate;

FIG. 10 is a fragmentary plan view of an alternative embodiment of the filter plate;

FIG. 11 is a plan view of a 24-well filter plate which is essentially one-half the plate of the FIG. 7 embodiment;

FIG. 12 is a plan view of an 8-well filter plate;

FIG. 13 is a cross-sectional view of the 8-well filter plate of FIG. 12 taken along the section line 13—13 in FIG. 12; and FIG. 14 is a fragmentary cross-sectional view of a system including a cluster well-plate, filter well plate and cover.

DETAILED DESCRIPTION

Figure 1:
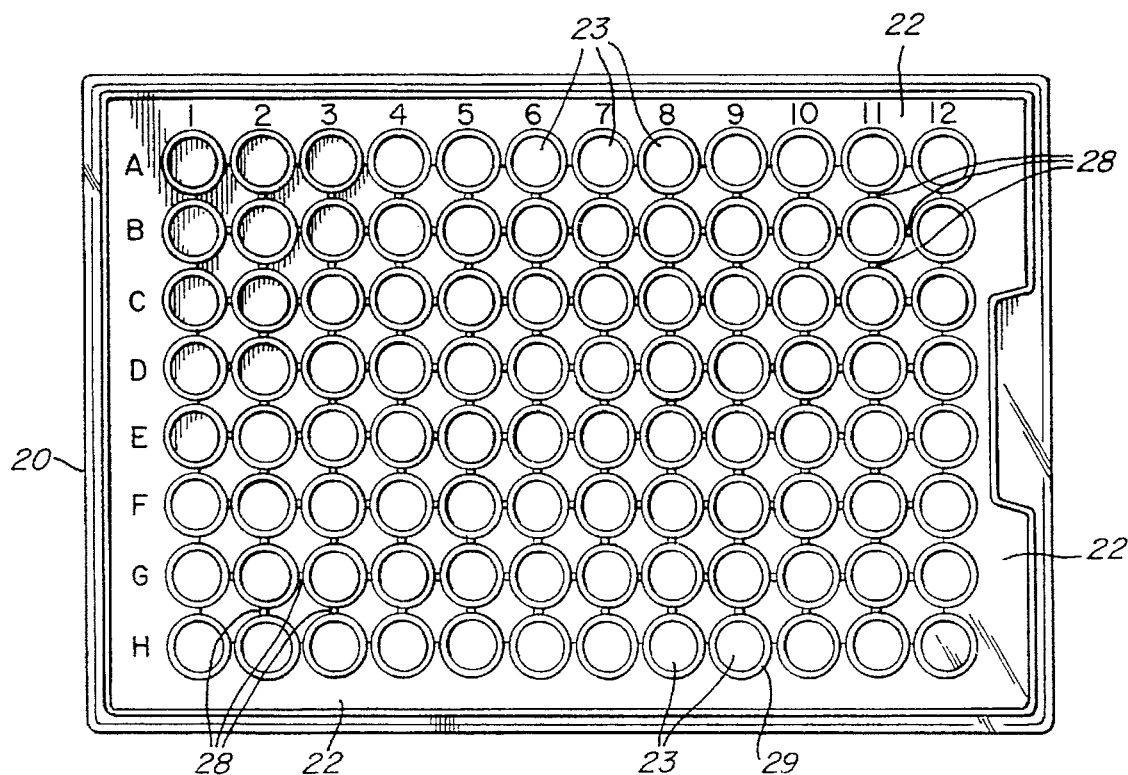
FIG. 1 is a plan view of a prior art 96-well cluster plate with its wells and overall dimensions conforming to the standardized format adopted by industry.
Figure 1A:
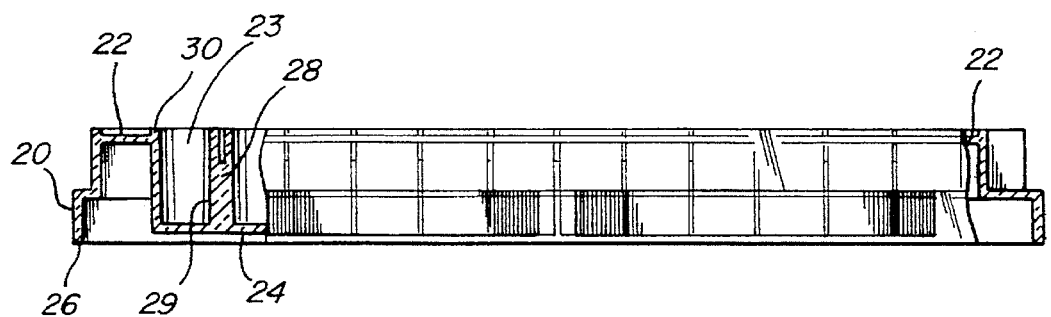
FIG. 1A is a side elevation view, partly, in section, of the prior art standardized plate shown in FIG. 1.

In FIGS. 1 and 1A, an example of a standard 96-well plate is shown. Its overall height, width, and length dimensions are standardized at 0.560, 3.370 and 5.035 inches, respectively. The plate includes a surrounding skirt 20, an upper peripheral panel 22, and an array of wells 23 arranged in 12 rows of eight wells each to provide 96 identical wells in the plate. The 12 rows of wells are numbered along the upper margin of the plate as shown in FIG. 1 (rows 1–12), and the separate wells 23 in each row are identified by the letters A–H along the left margin of that plate. The numbered rows and lettered wells correspond to the X and Y coordinates. The peripheral panel 22 of the plate extends between the skirt 20 and the periphery of the wells on the outside of the 96-well matrix as is evident in FIG. 1.

Industry standards prescribe that the center lines of the rows be spaced apart 0.355 inches, and similarly, the centers of adjacent wells 23 in the same row be spaced apart the same distance, namely 0.355 inches. The bottoms of the wells in the standard multi-well plate shown in FIGS. 1 and 1A are closed by a single lower panel 24 whose bottom surface lies above the plane of the lower edge 26 of the skirt 20. The well matrix is given rigidity by bridges 28 that extend between the side walls 29 of adjacent wells where they approach tangency. The upper edge 30 of each well extends above the plane of the peripheral panel 22. The cluster plates are molded of plastic and are provided with transparent covers (not shown) with drip rings to control water loss by evaporation while allowing gas exchange and maintaining sterility.

As described above, the standardization of the format of the 96-well plate has led to the development of a substantial variety of auxiliary equipment to perform liquid transfers to and from the wells, to transmit light through the wells and to read colorimetric changes or chemiluminescence in individual wells, and many other functions. The liquid transferring equipment is either hand or robotic operated, and much of the equipment used for analyzing the contents of the wells is automated and instrumented to record, analyze and manipulate the data recorded. The present invention includes, inter alia, a multi-well cluster dish having substantially larger wells than those found in the standard 96-well cluster but which is compatible with the auxiliary equipment designed for that format.

In FIGS. 2–6, the multi-well, cluster plate of this invention is shown. The plate 40 includes a peripheral skirt 42 which precisely conforms to the dimensions of the skirt 20 of the standard 96-well plate of FIGS. 1 and 1A. Furthermore, the overall height, length and width dimensions of the plate 40 are the same as that of the plate shown in FIGS. 1 and 1A. An array of wells 44 are provided in the plate 40, which in the embodiment shown are 48 in number, and their pattern is different from that of the 96-well plate shown in FIG. 1. In accordance with the present invention, the wells 44 are arranged in 12 rows parallel to the Y coordinate (the odd numbered rows 1, 3, 5, 7, 9 and 11 are numbered along the upper side of the plate as viewed in FIG. 2 while the even numbered rows 2, 4, 6, 8, 10 and 12 are numbered along the lower edge as viewed in that figure). The 12 rows are spaced apart the same distance as the 12 rows in the standard plate, namely, 0.355 inches. Row 1 has its center line disposed the same distance from the skirt at the left side of the plate as viewed in FIG. 2 as is the center line of row 1 of the wells from the skirt on the left margin in the 96-well plate as viewed in FIG. 1. That distance is standardized at 0.565 inches by the industry. Each row has four wells with the wells in adjacent rows staggered from one another. For purposes of this description, the rows of wells parallel to the X coordinate are identified along the left edge of the plate 40 as A–H.

The four wells 44B, 44D, 44F, and 44H in row 1 in the embodiment of FIG. 2 are oriented so that their centers conform precisely to the location of the centers of the wells B, D, F, and H of row 1 in the standard format 96-well plate of FIG. 1. Thus, the centers of those wells are disposed 0.710 inches apart. The wells in row 2 of the present invention, whose common center line is 0.355 inches from the center line of row 1, have their centers aligned with wells A, C, E, and G of row 2 in the standard format of FIG. 1. Thus, the centers of the wells in row 2 lie midway between the centers of the wells in row 1 and the wells 44 in alternate numbered rows of the plate 40 are aligned with one another in the long dimension of the plate.

A peripheral panel 46 extends inwardly from the skirt 42 to the outer portion of each of the wells at the ends of the rows both in the X and Y directions and, therefore, corresponds to the peripheral panel 22 in the 96-well array. As in that arrangement, the bottoms of the wells are closed by a single panel 48 which is disposed above the lower edge 50 of the skirt 42 (see FIGS. 5 and 6).

It will be noted in FIG. 5 that the wells 44 are arranged so that at their point of tangency, the adjacent wells share a common wall as may be noted at 52. The same relationship exists between adjacent wells throughout the matrix. This arrangement maximizes the diameter of the separate wells 44 and provides certain advantages as described more fully below.

It will be appreciated from the foregoing that the center of each well in the 48-well matrix shown in FIG. 2 corresponds to the center of one of the wells in the 96-well matrix in FIG. 1. More specifically, the four wells in each of rows 1, 3, 5, 7, 9, and 11 (lateral rows B, D, F, and H) have centers which correspond to the centers of wells B, D, F, and H in rows 1, 3, 5, 7, 9, and 11 in the 96-well format. Similarly, the centers of the four wells in rows 2, 4, 6, 8, 10 and 12 in the matrix of FIG. 2 correspond to the centers of wells A, C, E, and G of rows 2, 4, 6, 8, 10, and 12 in the standard format of FIG. 1. Therefore, the cluster plate of FIGS. 2–6 can be used on auxiliary equipment designed for use with cluster dishes having the standard 96-well format. An example of such equipment is the eight-channel pipetter shown in U.S. Pat. No. 4,599,220, dated Jul. 8, 1986, entitled MULTI-CHANNEL PIPETTER. The multi-channel pipetter shown, like other such pipetters available, includes a single row composed of eight pipettes that are actuated by a common mechanism within the device. Each of the pipettes includes a holder for carrying disposable tips and which are that are spaced apart, center to center, 0.355 inches, the same distance which separates the centers of the wells in the standard plate shown in FIGS. 1 and 1A. It will be appreciated that simply by removing alternate tips in the pipetter, it may be used to transfer liquids to and from any of the four-well rows in the cluster plate of FIGS. 2–6. Similarly, other auxiliary equipment may be used with the embodiment of the cluster well plate shown. A transparent cover with drip rings to match the wells, with space to provide gas exchange while controlling water loss, and maintaining sterility is provided for the cluster plate. Such a cover is suggested in the system shown in FIG. 14.

Figure 4:
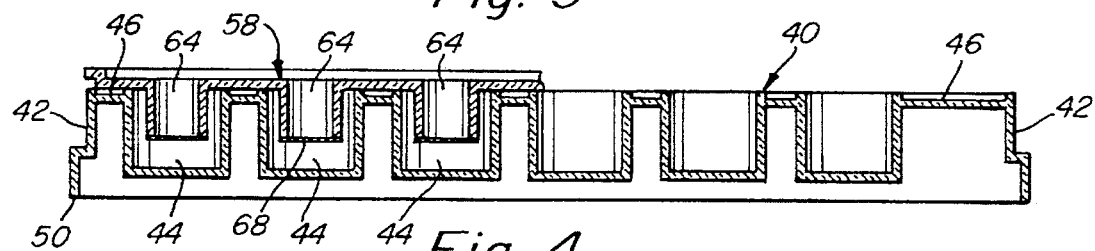
FIG. 4 is a fragmentary cross-sectional view of the 48-well cluster plate of FIG. 2 taken along the section lines 4—4 in FIG. 2 and further showing a filter plate of the type shown in FIG. 7 disposed on it.

In FIGS. 7–13, a number of filter plates are shown which are designed for use with the cluster plate of FIG. 2. In FIG. 4, this arrangement is suggested. In FIGS. 7–9, a 48-filter plate 58 is shown comprising a top wall 60, a peripheral lip 62 that extends about the top wall 60 and an array of filter wells 64. The centers of the wells 64 are spaced apart precisely as the centers of the wells in the plate of FIG. 2, and the filter plate is designed to be superimposed on the cluster plate with the filter wells 44 extending into and centered with the wells 44 as is described below (see FIG. 4). Each of the wells 64 includes a generally cylindrical side wall 66 and a filter 68 that defines the bottom wall of the well. The filter material may be anything from a dialysis membrane or a microporous membrane up to a 12 micron screen depending upon th particular procedure to be conducted. In this embodiment, the individual wells are connected to one another by the top wall 60 which has large openings 69 through the plate between the various wells. The openings 69 provide access to the wells 44 of the cluster plate with which the filter plate is used so that media or other liquid may be added to or removed from each of the wells while the filter plate remains in place.

Each of the filter wells 64 preferably has an internal diameter of approximately 0.250 inches, the same as the internal diameter of the wells 23 in the standard 96-well plate. The outer diameter of each filter well 64 is approximately 0.320 inches, which is significantly smaller than the inner diameter of the reservoir wells 44 in the cluster plate 40. Therefore, the filter wells 64 are sized to fit freely into the reservoir wells of the cluster plate with a substantial gap between the outer surface of wall 66 of the filter wells 64 and the inner surface of walls 47 of the reservoir wells. In the embodiment of the cluster dish shown in FIG. 2, the inner diameter of the reservoir wells is approximately 0.472 inches.

The openings 69 extend between each pair of adjacent wells and their width in FIG. 7 is shown equal to the inner diameter of the wells 64. In FIG. 10, a variation is shown in which the openings 69' are equal in width to the outer diameter of the wells.

A variety of different techniques may be provided for positioning the filter plate 58 of FIGS. 7–9 on the cluster plate so that the filter wells 64 are centered with the wells 44. One such arrangement is shown in detail in FIG. 9A. It will be noted that on the outer surface of the cylindrical wall 66 of the well 64 shown, a number of stepped shoulders 70 are provided about the well periphery. The diameter of the circle described by the smaller steps 72 is very slightly less than the inner diameter of the reservoir wells 44 so that the steps will engage the inner surface of the upper portion of the walls 46 of the wells 44. The diameter of the circle described by the upper, larger steps 76 of the shoulder exceeds the inner diameter of the cylindrical walls 46 of the wells 44 and, therefore, they limit the extent to which the filter wells 64 extend into the wells 44. It will be appreciated that the stepped shoulders 70 shown in FIG. 9A may be provided on all or just a few of the filter wells in the plate 58, and in either case, the shoulders will serve to center the plate and its filter wells 64 with respect to the cluster plate 40 and its wells 44.

While the stepped shoulders 70 are shown to center the wells and plates with one another, other techniques may be employed to serve the same purpose. For example, raised pins (not shown) may be molded into the surface of the peripheral panel 46 of the cluster plate of FIG. 2, which register with corresponding recesses (not shown) provided in the lower surface of the panel 60 of the filter plate 58. Four such pins on the panel 46 of the cluster plate typically located adjacent the corners with corresponding recesses in the upper panel 60 may serve both to insure the alignment of the filter wells 64 with the reservoir wells 44 and to establish a prescribed orientation between the filter and cluster plates.

In FIG. 11, a 24-filter well plate arrangement 80 is shown which essentially is simply one-half the plate of FIG. 7. The 24-filter well plate may otherwise be constructed in precisely the same fashion as the plate of FIG. 7. However, along one edge 82 of the plate 80, the lip 62 is omitted so that the plate may conveniently be used with another identical plate abutting one another along edges 82 when a 48-well array is desired.

It is also contemplated that this invention may be embodied in a 12-filter well, 8-filter well, 4-filter well, and single-filter well, and each may essentially contain the same characteristics as the plate described in detail above. An 8-well filter plate 90 is shown in FIGS. 12–13. In each instance, the wells of the plate are provided with impervious side walls molded of plastic as an integral part of the filter plate, and the bottom filter walls may be made of screening, membrane or other like material having openings of a particular size selected for the particular function to be performed. The sides of the plate 90 are relieved as at 92 to provide access to the cluster plate wells 44.

In copending application Ser. No. 06/841,562, a number of typical applications for the filter wells in combination with a cluster plate are described. A typical application is for growing tissue cultures. The assembly for carrying out this procedure is shown in FIG. 14. The filter wells may be used by adding media to the cluster plate reservoir wells, and thereafter placing the filter well plate over the cluster plate with the lower portions of the filter wells immersed in the media in the reservoir wells. Thereafter, media and cells are deposited in each of the filter wells, and the assembly may be closed by the cover as shown in FIG. 14. Additional media may be introduced directly into the filter wells through their open tops in the filter plate, and media may also be added to the reservoir wells in the cluster plate through the openings such as 69 or 69' in the filter well plate between the individual filter wells. After the layer of tissue has grown on the filter membrane, the filter plate may be removed and the contents of the reservoir wells may be analyzed on the appropriate auxiliary equipment provided for the 96-well plate.

It is also contemplated that the filter plates of FIGS. 7–13 may be used with a common reservoir 100 as suggested in FIG. 8 to grow tissue culture monolayers in multiples prior to using the cluster plates for analysis purposes. For that purpose, the common reservoir 100 shown in FIG. 8 may be filled with a particular media and the filter plate 58 (or other plate) may thereafter be placed on it with the rim 62 of panel 60 resting on the upper edge 92 of the reservoir. The rim 62 will serve to center the filter plate on the reservoir 100, and it will also facilitate lifting the plate off the reservoir.

It is desirable that the diameter of the membrane filters defining the bottom wall of each of the filter wells be the same as the diameter of the wells in the 96-well format for standardization. The surface area of the membrane should be sufficiently large to provide tissue samples that can be conveniently handled. It is also desirable that the capacity of the reservoir wells minus the volume occupied by the filter wells generally equal the inner capacity of the filter wells so that equal quantities of media may be placed in each. The large size of the cluster dish wells of this invention enables that equality to be achieved.

From the foregoing description, it will be appreciated that the present invention enables multiple samples to be grown or manipulated on a filter plate with a large number of individual wells. The wells may be either permanently attached to each other or attached so that individual wells can be separated from the others. A frangible strip of wells as shown in copending application Ser. No. 06/923906. The multi-well filter plate impedes capillary action from occurring between the filter well and the cluster well side walls, and the system can be used on 96-well auxiliary equipment. The membrane diameter of the individual wells is preferably the same as the diameter of the bottom wall in a standard 96-well plate. Therefore, the membrane may be handled easily. The cluster plate can be loaded and aspirated with 8, 12 or 96-well handling equipment that is presently available. The system enables 96-well ELISA test readers to be used in combination with the multi-well filter plates for applications such as chemotaxis studies, proliferation assays, cell uptake analysis, and diagnostic tests where membranes are used for separation, sorting, affinity binding, etc. The 48-well cluster plate can be read in a 96-well reader with large volume wells for tests that require a larger volume than can be handled in the traditional 96-well plate.

The filter material used in the filter plates may vary widely, from 0.01 to 25 microns and from 100 to 10 million Daltons. Generally, any thin film material, porous or non-porous, which can be bonded to the plastic filter well bottom may be used.

Having described this invention in detail, those skilled in the art will appreciate that numerous modifications may be made thereof without departing from the spirit of this invention. Therefore, it is not intended that the scope of this invention be limited to specific embodiments illustrated and described. Rather, the scope of this invention is to be determined by the appended claims and their equivalents.

What is claimed is:

1. A multi-well cluster system designed for use with auxiliary equipment that loads and unloads precise volumes of liquid and/or reads the light transmitted through or emanating from each of the wells in a standard format 96-well plates comprising:

a cluster plate having a matrix of wells, fewer in number than 96, forming at least one row of wells wherein the wells are spaced apart, center to center, a distance which is a whole number multiple of the distance between adjacent wells in the 96 well standard format and wherein the cluster plate wells are each aligned with a different wells in the standard format enabling the cluster plate to be used with said auxiliary equipment, the diameters of each of the wells in the cluster plate being greater than the center to center distance of adjacent wells in the standard 96-well.

2. A multi-well cluster system as described in claim 1 wherein the matrix of wells comprises 48 wells with their centers arranged in 12 parallel rows of 4 wells each and with the centers of the wells in each row being staggered with respect to the centers of the wells in the adjacent rows.

3. A multi-well system as defined in claim 2 wherein the cluster plate has overall length and width dimensions equal to the corresponding dimensions of a 96-well standard format plate.

4. A multi-well system as defined in claim 1 wherein the cluster plate has overall length and width dimensions equal to the corresponding dimensions of a 96-well standard format plate.

5. A multi-well cluster system as described in claim 3 wherein the system includes a second plate having a plurality of wells each having a solid side wall and a bottom wall made of porous material, said wells in the second plate being spaced apart and sized to fit into separate wells in the cluster plate.

6. A multi-well cluster system as described in claim 1 wherein the system includes a second plate having a plurality of wells each having a solid side wall and a bottom wall made of porous material, said wells in the second plate being spaced apart and sized to fit into separate wells in the cluster plate.

7. A multi-well cluster system as defined in claim 6 wherein the wells in the porous plate are equal in number to and are in the same format as the wells in the cluster plate.

8. A multi-well cluster system as defined in claim 6 where in the cluster plate and porous plate each have 48 wells.

9. A multi-well cluster system as defined in claim 6 wherein the porous plate has half the number of wells as are in the cluster plate.

10. A multi-well cluster system as defined in claim 6 wherein the cluster plate has 48 wells.

11. A multi-well cluster system as defined in claim 10 wherein the porous plate has 24 wells.

12. A multi-well cluster system as defined in claim 10 wherein the porous plate has 12 wells.

13. A multi-well cluster system as defined in claim 10 wherein the porous plate has 8 wells.

14. A multi-well cluster system as defined in claim 10 wherein the porous plate has 4 wells.

15. A multi-well cluster system as defined in claim 10 wherein the porous plate has one well.

16. In a system as defined in claim 6, the diameter of each of said wells in the second plate being equal to the diameter of the wells in a standard 96-well cluster plate.

17. A system as defined in claim 6 wherein, a reservoir is provided for containing media wherein said reservoir is constructed to receive simultaneously all of the wells of the second plate.

18. In a system as defined in claim 6, said wells of the second plate being connected together by frangible connecting means so that they may be selectively broken away from other wells to which they are connected.

19. A system as defined in claim 6, wherein means are operatively connected to the cluster plate and the second plate for positioning the two together so that the wells of the second plate are aligned with the wells in the cluster plate.

20. A system as defined in claim 19, wherein said means operatively connected to the cluster plate and second plate establish a selected depth the wells of the second plate may extend into the cluster plate wells.

21. A multi-well cluster system as defined in claim 19 wherein the wells in the second plate are equal in number to and are in the same format as the wells in the cluster plate.

22. A multi-well cluster system as defined in claim 19 wherein the cluster plate has 48 wells.

23. A system as defined in claim 19, wherein means are provided in the second plate for providing access to the wells in the cluster plate and second plate while the second plate is positioned with its wells extending into the cluster plate wells.

24. A multi-well system as defined in claim 1 wherein the cluster plate has 48 wells.

25. A multi-well system as defined in claim 4 wherein
the center to center distance between adjacent wells in the same row is twice the center to center distance between adjacent wells in the 96-well format.

26. A multi-well cluster system as defined in claim 5 wherein the second plate has half the number of wells as are in the cluster plate.

* * * * *